US00RE41740E

(19) United States
(12) Reissued Patent
Okerlund et al.

(10) Patent Number: US RE41,740 E
(45) Date of Reissued Patent: Sep. 21, 2010

(54) MULTI-SECTOR BACK-OFF LOGIC ALGORITHM FOR OBTAINING OPTIMAL SLICE-SENSITIVE COMPUTED TOMOGRAPHY PROFILES

(75) Inventors: Darin Robert Okerlund, Muskego, WI (US); Mark Edward Woodford, Waukesha, WI (US); Edward Henry Chao, Sauk City, WI (US); Rajendra Kurady, Waukesha, WI (US)

(73) Assignee: General Electric Company, Schenectady, NY (US)

(21) Appl. No.: 11/706,836

(22) Filed: Feb. 14, 2007

(Under 37 CFR 1.47)

Related U.S. Patent Documents

Reissue of:
(64) Patent No.: 6,873,675
Issued: Mar. 29, 2005
Appl. No.: 10/323,256
Filed: Dec. 18, 2002

(51) Int. Cl.
*A61B 6/00* (2006.01)

(52) U.S. Cl. ..... 378/4; 378/8; 378/901
(58) Field of Classification Search ..... 378/4–20
See application file for complete search history.

(56) References Cited

U.S. PATENT DOCUMENTS 6,134,293 A * 10/2000 Guendel ..... 378/4
6,154,516 A * 11/2000 Heuscher et al. ..... 378/15
6,307,910 B1 * 10/2001 Acharya et al. ..... 378/4
6,393,091 B1 * 5/2002 Slack et al. ..... 378/8
6,504,893 B1 * 1/2003 Flohr et al. ..... 378/8
6,587,539 B2 * 7/2003 Oikawa ..... 378/19
6,628,742 B2 * 9/2003 Pan et al. ..... 378/8
6,665,370 B2 * 12/2003 Bruder et al. ..... 378/15
2002/0021785 A1 * 2/2002 Toth et al. ..... 378/147
2002/0136350 A1 * 9/2002 Pan et al. ..... 378/8
2003/0185337 A1 * 10/2003 Hsieh ..... 378/4
2004/0017881 A1 * 1/2004 Cesmeli et al. ..... 378/4

* cited by examiner

*Primary Examiner*—Edward J Glick
*Assistant Examiner*—Alexander H Taningco
(74) *Attorney, Agent, or Firm*—ZPS Group, SC

(57) ABSTRACT

A multi-sector back-off logic algorithm for obtaining optimal slice-sensitive computed tomography ("CT") profiles. The systems and methods of the present invention improving the temporal resolution of a CT system by checking for Z location errors between sectors and automatically backing-off to an alternative multi-sector algorithm when necessary (i.e., selecting an optimized maximum number of sectors to reconstruct), providing less Z location error. Based upon this Z location error, the systems and methods of the present invention also calculating the maximum number of sectors that should be used for reconstruction "on-the-fly" (i.e., on a per image basis across an entire series of images). These systems and methods utilizing the Recommended Protocol for Cardiac Reconstruction Algorithms.

38 Claims, 4 Drawing Sheets

MULTI-SECTOR BACK-OFF LOGIC ALGORITHM FOR OBTAINING OPTIMAL SLICE-SENSITIVE COMPUTED TOMOGRAPHY PROFILES

Matter enclosed in heavy brackets [ ] appears in the original patent but forms no part of this reissue specification; matter printed in italics indicates the additions made by reissue.

FIELD OF THE INVENTION

The present invention relates generally to computed tomography ("CT") systems and methods. More specifically, the present invention relates to a multi-sector back-off logic algorithm for obtaining optimal slice-sensitive CT profiles, especially for cardiac applications.

BACKGROUND OF THE INVENTION

Computed tomography ("CT") systems are often used to image the heart and cardiovasculature. The data for a given image may be collected from multiple cardiac cycles using multiple sectors. This creates a number of challenges. In an ideal case, the multiple sectors used to reconstruct the heart and cardiovasculature overlap for a zero Z location error between sectors. This, however, is not always the case. For a relatively low heart rate and high pitch, for example, the sectors used to reconstruct the heart and cardiovasculature do not always overlap, resulting in a relatively large Z location error between sectors and relatively poor slice-sensitive profiles. Because of this, the data collected from multiple cardiac cycles may be too far apart, resulting in poor image quality.

Thus, what is needed are systems and methods that generate high temporal resolution images for cardiac CT applications while addressing the problem of bad images by checking for these Z location errors between sectors and automatically backing-off to an alternative multi-sector algorithm when necessary (i.e., selecting an optimized maximum number of sectors to reconstruct), providing less Z location error. What is also needed are systems and methods that, based upon this Z location error, calculate the maximum number of sectors that should be used for reconstruction "on-the-fly" (i.e., on a per image basis across an entire series of images). Preferably, these systems and methods utilize the Recommended Protocol for Cardiac Reconstruction Algorithms.

BRIEF SUMMARY OF THE INVENTION

Accordingly, the present invention provides a multi-sector back-off logic algorithm for obtaining optimal slice-sensitive computed tomography ("CT") profiles. The systems and methods of the present invention generate high temporal resolution images for cardiac CT applications and address the problem of bad images by checking for Z location errors between sectors and automatically backing-off to an alternative multi-sector algorithm when necessary (i.e., selecting an optimized maximum number of sectors to reconstruct), providing less Z location error. Based upon this Z location error, the systems and methods of the present invention also calculate the maximum number of sectors that should be used for reconstruction "on-the-fly" (i.e., on a per image basis across an entire series of images). These systems and methods utilize the Recommended Protocol for Cardiac Reconstruction Algorithms.

In one embodiment of the present invention, a computed tomography method includes determining a maximum Z location error and determining a weighted average Z location error. The computed tomography method also includes selecting a threshold value associated with the maximum Z location error and the weighted average Z location error. The computed tomography method further includes prescribing an N+1 sector reconstruction algorithm. If the maximum Z location error is less than or equal to the threshold value or the weighted average Z location error is less than or equal to the threshold value, the computed tomography method includes performing an N+1 sector reconstruction. If the maximum Z location error exceeds the threshold value or the weighted average Z location error exceeds the threshold value, the computed tomography method includes prescribing an N sector reconstruction.

In another embodiment of the present invention, a computed tomography method for obtaining optimal slice-sensitive profiles includes determining a maximum Z location error associated with a computed tomography system and determining a weighted average Z location error associated with the computed tomography system. The computed tomography method also includes selecting a threshold value associated with the maximum Z location error and the weighted average Z location error. The computed tomography method further includes prescribing an N+1 sector reconstruction algorithm. If the maximum Z location error is less than the threshold value or the weighted average Z location error is less than the threshold value, the computed tomography method includes performing an N+1 sector reconstruction. If the maximum Z location error exceeds the threshold value or the weighted average Z location error exceeds the threshold value, the computed tomography method includes prescribing an N sector reconstruction.

In an further embodiment of the present invention, an imaging method for obtaining optimal slice-sensitive profiles includes determining a maximum Z location error associated with an imaging system and determining a weighted average Z location error associated with the imaging system. The imaging method also includes selecting a threshold value associated with the maximum Z location error and the weighted average Z location error. The imaging method further includes prescribing an N+1 sector reconstruction algorithm. If the maximum Z location error is less than the threshold value or the weighted average Z location error is less than the threshold value, the imaging method includes performing an N+1 sector reconstruction. If the maximum Z location error exceeds the threshold value or the weighted average Z location error exceeds the threshold value, the imaging method includes prescribing an N sector reconstruction.

In a still further embodiment of the present invention, a computed tomography system includes a computed tomography scanner, a first algorithm operable for determining a maximum Z location error associated with the computed tomography system, and a second algorithm operable for determining a weighted average Z location error associated with the computed tomography system. The computed tomography system also includes a third algorithm operable for selecting a threshold value associated with the maximum Z location error and the weighted average Z location error. The computed tomography system further includes means for prescribing an N+1 sector reconstruction algorithm. The computed tomography system still further includes a fourth algorithm operable for, if the maximum Z location error is less than the threshold value or the weighted average Z location error is less than the threshold value, performing an N+1 sector reconstruction, and wherein the fourth algorithm is further operable for, if the maximum Z location error exceeds the threshold value or the weighted average Z location error exceeds the threshold value, prescribing an N sector reconstruction.

In a still further embodiment of the present invention, an imaging system includes an imaging scanner, a first algorithm operable for determining a maximum Z location error associated with the imaging system, and a second algorithm operable for determining a weighted average Z location error associated with the imaging system. The imaging system also includes a third algorithm operable for selecting a threshold value associated with the maximum Z location error and the weighted average Z location error. The imaging system further includes means for prescribing an N+1 sector reconstruction algorithm. The imaging system still further includes a fourth algorithm operable for, if the maximum Z location error is less than the threshold value or the weighted average Z location error is less than the threshold value, performing an N+1 sector reconstruction, and wherein the fourth algorithm is further operable for, if the maximum Z location error exceeds the threshold value or the weighted average Z location error exceeds the threshold value, prescribing an N sector reconstruction.

DETAILED DESCRIPTION OF THE INVENTION

Figure 1:
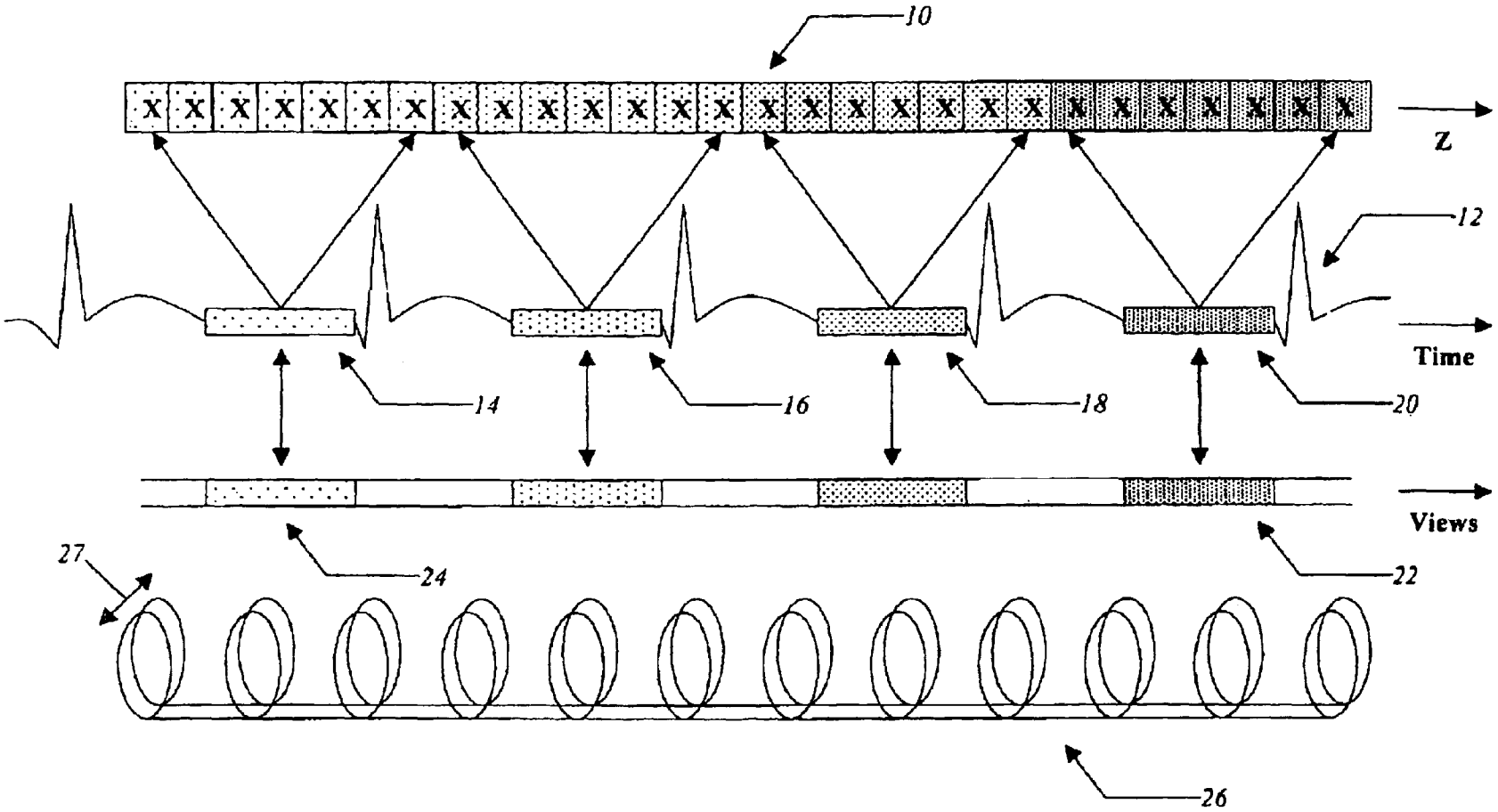
FIG. 1 is a schematic diagram illustrating a retrospectively EKG-gated reconstruction associated with the systems and methods of the present invention.

The systems and methods of the present invention allow for the creation of relatively high temporal resolution images for cardiac applications while addressing the problem of the generation of bad images due to relatively large Z location errors between sectors that are used for reconstruction. In general, the algorithm of the present invention is based upon the measurement of maximum Z location error ("ME") and weighted average Z location error ("WE") and determining how far these measurements are from predetermined limits.

The computation of the Z location error, ME, and WE includes a number of steps beginning with calculating half the detector coverage (i.e., the distance from the center of the detector to the center of the outer row). This is done using the following equation:

$$\text{half the detector coverage}=[(\text{num_rows}/2)-1]*\text{detector width}. \quad (1)$$

Next, the Z location error is computed for each sector. This is done by finding the Z location of the center view in the table space and calculating upper ("maximum") limit and the lower ("minimum") limit that the detector may cover at this particular Z location. The maximum limit and the minimum limit are given by:

$$\text{maximum limit}=\text{center Z location}+\text{half the detector coverage}, \quad (2)$$

$$\text{minimum limit}=\text{center Z location}-\text{half the detector coverage}. \quad (3)$$

The Z location error is computed for each sector using the following algorithm and is a signed value:

$$\text{if Z location}<\text{lower limit, Z location error}=\text{lower limit}-\text{Z location}(4)$$

$$\text{if Z location}>\text{upper limit, Z location error}=\text{upper limit}-\text{Z location}(5)$$

$$\text{if lower limit}<\text{Z location}<\text{upper limit, Z location error}=0. \quad (6)$$

Next, the maximum error between the upper most and lower most error sectors is calculated. This also involves calculating the maximum and minimum errors within the set of sectors and the maximum error spread. The maximum error spread is given by:

$$\text{maximum error spread}=\text{maximum error}-\text{minimum error}-\max(Zi-Z_{desired})-\min(Zi-Z_{desired}). \quad (7)$$

Next, WE is calculated using the average error weighted by the number of views in each sector:

$$WE=\text{total error over all sectors/total view over all sectors}=\text{sum}(0,\text{sector}-1)|Zi-Z_{desired}|*Wi. \quad (8)$$

The percentage of image locations, or images, that fall into the gap is given by gap/(gap+overlap).

Referring to FIG. 1, in one embodiment of the present invention, a retrospectively EKG-gated reconstruction is illustrated. The retrospectively EKG-gated reconstruction provides a plurality of image locations 10 that vary as a function of Z location associated with predetermined points along an EKG cycle 12 that vary as a function of time. The predetermined points along the EKG cycle 12 include, for example, a first cycle 14, a second cycle 16, a third cycle 18, and a fourth cycle 20. The reconstruction algorithm of the present invention provides a continuous view stream 22 consisting of a plurality of view regions 24 utilized by the reconstruction algorithm. These view regions 24 correspond to the first cycle 14, the second cycle 16, the third cycle 18, and the fourth cycle 20. A plurality of detector rows 27 are used to obtain images as part of a low-pitch helical scan 26.

Figure 2:
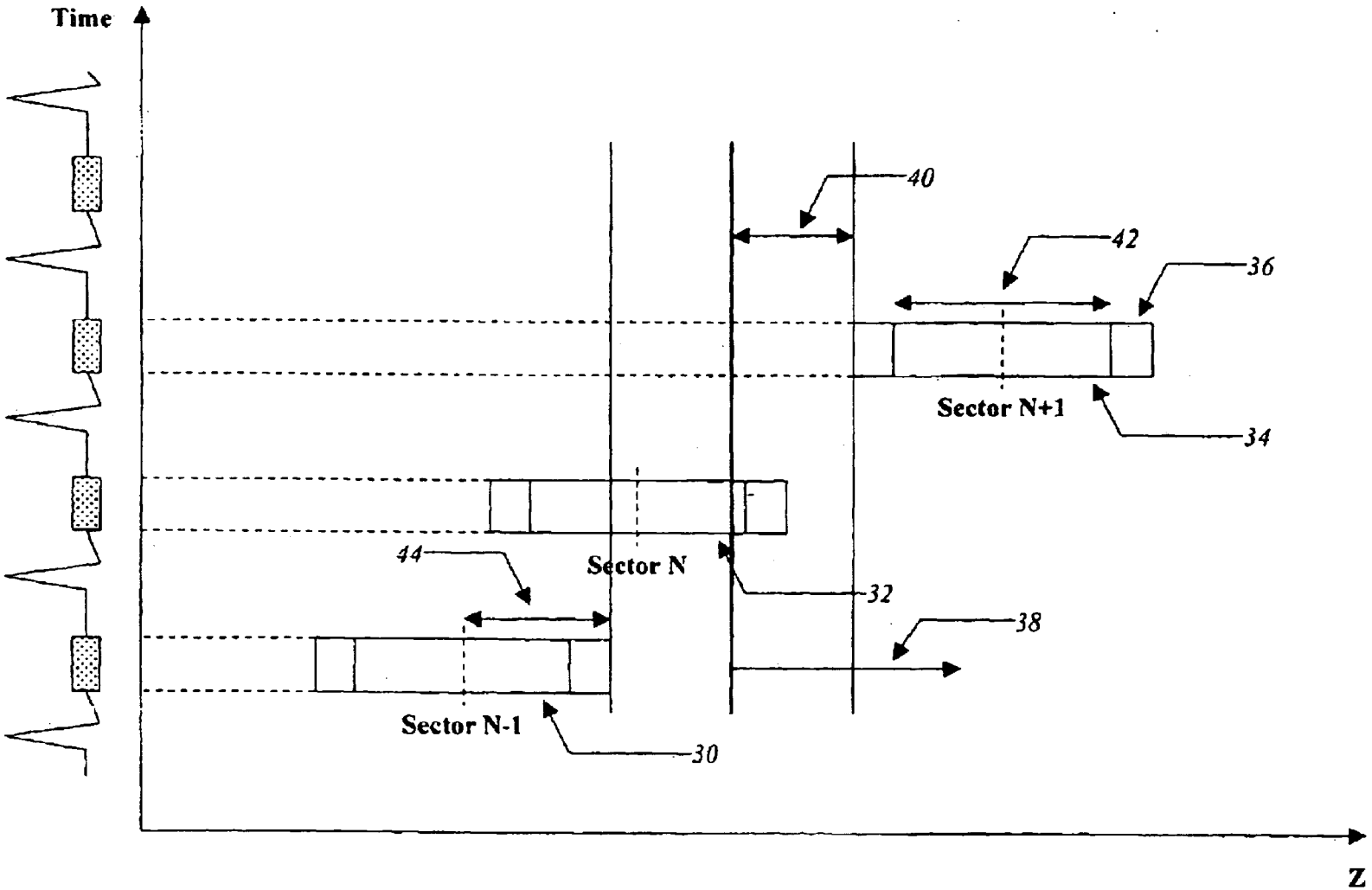
FIG. 2 is a graph illustrating the Z location error concepts associated with the systems and methods of the present invention.

In another embodiment of the present invention, the Z location error concepts described above are illustrated in FIG. 2. FIG. 2 shows a plurality of sectors, including a sector N−1 30, a sector N 32, and a sector N+1 34. Each sector includes a tolerance level 36. The Z location for a given image 38 and a Z location error >0 are also shown. Further, the half detector coverage 42 (i.e., 1.5 detector for a 4-row configuration, 3.5 detector for an 8-row configuration, 7.5 detector for a 16-row configuration) and the range 44 are also shown.

As described above, the multi-sector back-off logic algorithm for obtaining optimal slice-sensitive CT profiles of the present invention is based upon deciding the maximum number of sectors to reconstruct in a given situation. This determination is made based upon how far two given sectors are separated with respect to the Z location. The algorithm begins with a predetermined number of sectors and, based upon the maximum Z location error and the weighted average Z location error, backs off to a lesser number of sectors until images may be generated with minimum error. This algorithm is illustrated in FIG. 3.

Figure 3:
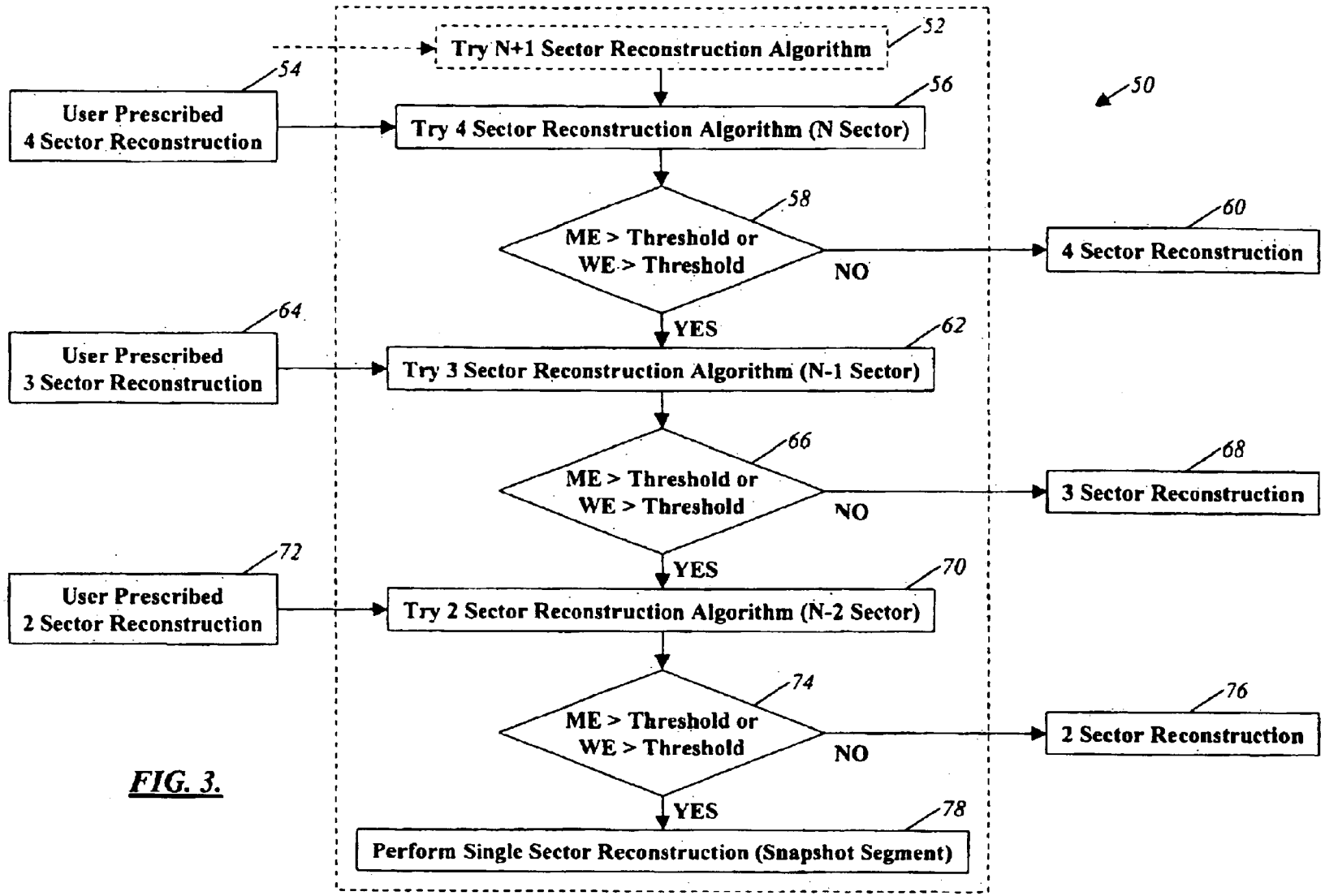
FIG. 3 is a flow chart illustrating one embodiment of the multi-sector back-off logic algorithm for obtaining optimal slice-sensitive CT profiles of the present invention.

Referring to FIG. 3, in a further embodiment of the present invention, the multi-sector back-off logic algorithm for obtaining optimal slice-sensitive CT profiles of the present invention 50 begins with the "auto burst" algorithm 50 trying an N+1 or N sector reconstruction algorithm 52,56.

For example, a user may prescribe a four sector reconstruction 54 and the auto burst algorithm 50 may try a four sector (N sector) reconstruction algorithm 56. If ME is less than the threshold or WE is less than the threshold 58, then a four sector reconstruction is performed 60. If ME exceeds the threshold or WE exceeds the threshold 58, then the auto burst algorithm 50 tries a three sector (N−1 sector) reconstruction algorithm 62. This is also the starting point if the user prescribes a three sector reconstruction 64. If ME is less than the threshold or WE is less than the threshold 66, then a three sector reconstruction is performed 68. If ME exceeds the threshold or WE exceeds the threshold 66, then the auto burst algorithm 50 tries a two sector (N−2 sector) reconstruction algorithm 70. This is also the starting point if the user prescribes a two sector reconstruction 72. If ME is less than the threshold or WE is less than the threshold 74, then a two sector reconstruction is performed 76. If ME exceeds the threshold or WE exceeds the threshold 74, then the auto burst algorithm 50 performs a single sector reconstruction 78 (i.e., a snapshot segment).

Figure 4:
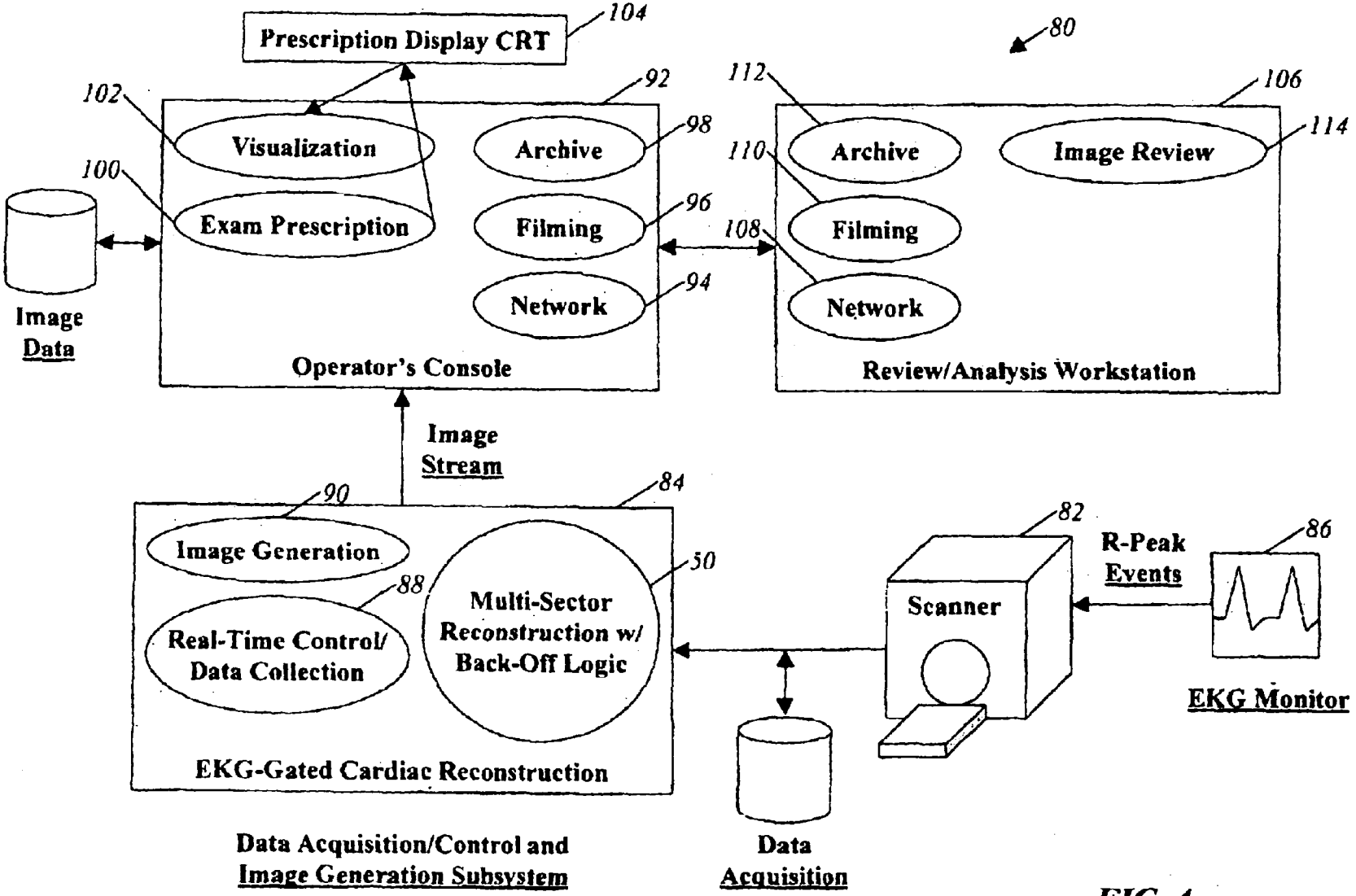
FIG. 4 is a schematic diagram illustrating one embodiment of a computed tomography ("CT") system incorporating the multi-sector back-off logic algorithm for obtaining optimal slice-sensitive CT profiles of the present invention.

Referring to FIG. 4, in a still further embodiment of the present invention, a CT system 80 incorporating the multi-sector back-off logic algorithm for obtaining optimal slice-sensitive CT profiles 50 includes a CT scanner 82 coupled to a data acquisition/control and image generation sub-system 84. Preferably, the CT scanner 82 is also coupled to an EKG monitor 86 or the like operable for measuring R-peak events or the like. The data acquisition/control and image generation subsystem 84 may be operable for performing, for example, an EKG-gated cardiac reconstruction. In order to do this, the data acquisition/control and image generation subsystem 84 includes a real-time control/data collection algorithm 88, the auto burst algorithm 50, and an image generation algorithm 90. The data acquisition/control and image generation subsystem 84 is operable for transmitting an image stream to an operator's console 92 or the like including a network component 94, a filming component 96, an archive component 98, an exam prescription component 100, and a visualization component 102. The exam prescription component 100 and the visualization component 102 may be associated with a prescription display CRT 104 or the like. The operator's console 92 is coupled to a review/analysis workstation 106 also including a network component 108, a filming component 110, and an archive component, as well as an image review component 114.

It is apparent that there has been provided, in accordance with the systems and methods of the present invention, a multi-sector back-off logic algorithm for obtaining optimal slice-sensitive CT profiles. Although the systems and methods of the present invention have been described with reference to preferred embodiments and examples thereof, other embodiments and examples may perform similar functions and/or achieve similar results. All such equivalent embodiments and examples are within the spirit and scope of the present invention and are intended to be covered by the following claims.

What is claimed is:

1. A computed tomography method, comprising:

determining a maximum Z location error;

determining a weighted average Z location error;

selecting a threshold value associated with the maximum Z location error and the weighted average Z location error;

prescribing an N+1 sector reconstruction algorithm;

if the maximum Z location error is less than the threshold value or the weighted average Z location error is less than the threshold value, performing an N+1 sector reconstruction; and if the maximum Z location error exceeds the threshold value or the weighted average Z location error exceeds the threshold value, prescribing an N sector reconstruction.

2. The computed tomography method of claim 1, further comprising, if [the] *a second* maximum Z location error is less than the threshold value or [the] *a second* weighted average Z location error is less than the threshold value, performing an N sector reconstruction.

3. The computed tomography method of claim 2, further comprising, if the *second* maximum Z location error exceeds the threshold value or the *second* weighted average Z location error exceeds the threshold value, prescribing an N−1 sector reconstruction.

4. The computed tomography method of claim 1, wherein the computed tomography method is used to perform cardiac imaging.

5. A computed tomography method for obtaining optimal slice-sensitive profiles, comprising:

determining a maximum Z location error associated with a computed tomography system;

determining a weighted average Z location error associated with the computed tomography system;

selecting a threshold value associated with the maximum Z location error and the weighted average Z location error;

prescribing an N+1 sector reconstruction algorithm;

if the maximum Z location error is less than the threshold value or the weighted average Z location error is less than the threshold value, performing an N+1 sector reconstruction; and if the maximum Z location error exceeds the threshold value or the weighted average Z location error exceeds the threshold value, prescribing an N sector reconstruction.

6. The computed tomography method of claim 5, further comprising, if [the] *a second* maximum Z location error is less than the threshold value or [the] *a second* weighted average Z location error is less than the threshold value, performing an N sector reconstruction.

7. The computed tomography method of claim 6, further comprising, if the *second* maximum Z location error exceeds the threshold value or the *second* weighted average Z location error exceeds the threshold value, prescribing an N−1 sector reconstruction.

8. The computed tomography method of claim 5, wherein the computed tomography method is used to perform cardiac imaging.

9. An imaging method for obtaining optimal slice-sensitive profiles, comprising:

determining a maximum Z location error associated with an imaging system;

determining a weighted average Z location error associated with the imaging system;

selecting a threshold value associated with the maximum Z location error and the weighted average Z location error;

prescribing an N+1 sector reconstruction algorithm;

if the maximum Z location error is less than the threshold value or the weighted average Z location error is less than the threshold value, performing an N+1 sector reconstruction; and if the maximum Z location error exceeds the threshold value or the weighted average Z location error exceeds the threshold value, prescribing an N sector reconstruction.

10. The imaging method of claim 9, further comprising, if [the] *a second* maximum Z location error is less than the threshold value or [the] *a second* weighted average Z location error is less than the threshold value, performing an N sector reconstruction.

11. The imaging method of claim 10, further comprising, if the *second* maximum Z location error exceeds the threshold value or the *second* weighted average Z location error exceeds the threshold value, prescribing an N−1 sector reconstruction.

12. The imaging method of claim 9, wherein the [computed tomography] *imaging* method is used to perform cardiac imaging.

13. A computed tomography system, comprising:

a computed tomography scanner;

a first algorithm operable for determining a maximum Z location error associated with the computed tomography system;

a second algorithm operable for determining a weighted average Z location error associated with the computed tomography system;

a third algorithm operable for selecting a threshold value associated with the maximum Z location error and the weighted average Z location error;

means for prescribing an N+1 sector reconstruction algorithm;

a fourth algorithm operable for, if the maximum Z location error is less than the threshold value or the weighted average Z location error is less than the threshold value, performing an N+1 sector reconstruction; and wherein the fourth algorithm is further operable for, if the maximum Z location error exceeds the threshold value or the weighted average Z location error exceeds the threshold value, prescribing an N sector reconstruction.

14. The computed tomography system of claim 13, wherein the fourth algorithm is further operable for, if [the] *a second* maximum Z location error is less than the threshold value or [the] *a second* weighted average Z location error is less than the threshold value, performing an N sector reconstruction.

15. The computed tomography system of claim 14, wherein the fourth algorithm is further operable for, if the *second* maximum Z location error exceeds the threshold value or the *second* weighted average Z location error exceeds the threshold value, prescribing an N−1 sector reconstruction.

16. The computed tomography system of claim 13, wherein the computed tomography system is used to perform cardiac imaging.

17. An imaging system, comprising:

an imaging scanner;

a first algorithm operable for determining a maximum Z location error associated with the imaging system;

a second algorithm operable for determining a weighted average Z location error associated with the imaging system;

a third algorithm operable for selecting a threshold value associated with the maximum Z location error and the weighted average Z location error;

means for prescribing an N+1 sector reconstruction algorithm;

a fourth algorithm operable for, if the maximum Z location error is less than the threshold value or the weighted average Z location error is less than the threshold value, performing an N+1 sector reconstruction; and wherein the fourth algorithm is further operable for, if the maximum Z location error exceeds the threshold value or the weighted average Z location error exceeds the threshold value, prescribing an N sector reconstruction.

18. The imaging system of claim 17, wherein the fourth algorithm is further operable for, if [the] *a second* maximum Z location error is less than the threshold value or [the] *a second* weighted average Z location error is less than the threshold value, performing an N sector reconstruction.

19. The imaging system of claim 18, wherein the fourth algorithm is further operable for, if the *second* maximum Z location error exceeds the threshold value or the *second* weighted average Z location error exceeds the threshold value, prescribing an N−1 sector reconstruction.

20. The imaging system of claim 17, wherein the imaging system is used to perform cardiac imaging.

*21. The computed tomography method of claim 1 wherein:*

*determining the maximum Z location error further comprises determining a first maximum Z location error and a second maximum Z location error; and*

*determining the weighted average Z location error further comprises determining a first weighted average Z location error and a second weighted average Z location error.*

*22. The computed tomography method of claim 5 wherein:*

*determining the maximum Z location error further comprises determining a first maximum Z location error and a second maximum Z location error; and*

*determining the weighted average Z location error further comprises determining a first weighted average Z location error and a second weighted average Z location error.*

*23. The imaging method of claim 9 wherein:*

*determining the maximum Z location error further comprises determining a first maximum Z location error and a second maximum Z location error; and*

*determining the weighted average Z location error further comprises determining a first weighted average Z location error and a second weighted average Z location error.*

*24. The computed tomography system of claim 13 wherein:*

*the first algorithm is further operable for determining a first maximum Z location error and a second maximum Z location error; and*

*the second algorithm is further operable for determining a first weighted average Z location error and a second weighted average Z location error.*

*25. The imaging system of claim 17 wherein:*

*the first algorithm is further operable for determining a first maximum Z location error and a second maximum Z location error; and*

*the second algorithm is further operable for determining a first weighted average Z location error and a second weighted average Z location error.*

*26. An imaging apparatus comprising:*

*an imager; and*

*a computer programmed to:*

*acquire scan data;*

*select a predetermined number of sectors corresponding to the scan data;*

*determine a multiple-sector Z location error corresponding to the predetermined number of sectors for a desired Z location;*

*select a Z location error threshold;*

*reconstruct an image from less than the predetermined number of sectors if the multiple-sector Z location error is above the Z location error threshold; otherwise*

*reconstruct an image from the predetermined number of sectors.*

*27. The imaging apparatus of claim 26 wherein the computer is further programmed to:*

*determine a Z location for each of the predetermined number of sectors;*

*determine a detector coverage associated with the imager;*

*calculate an upper limit and a lower limit of the detector coverage for each of the predetermined number of sectors; and*

*determine a single-sector Z location error for each of the predetermined number of sectors based on the respective Z location, the upper limit, and the lower limit of each sector.*

*28. The imaging apparatus of claim 27 wherein the computer is further programmed to:*

*set the single-sector Z location error for each sector equal to the lower limit minus the Z location, if the respective single-sector Z location is less than the lower limit;*

*set the single-sector Z location error for each sector equal to the upper limit minus the Z location, if the respective single-sector Z location is greater than the upper limit; otherwise*

*set the single-sector Z location equal to zero.*

*29. The imaging apparatus of claim 27 wherein the computer is further programmed to:*

*identify an upper-most Z location error sector of the predetermined number of sectors based on the single-sector Z location error of each sector;*

*identify a lower-most Z location error sector from the predetermined number of sectors based on the single-sector Z location error of each sector; and*

*determine the multi-sector Z location error by calculating a maximum Z location error based on the upper-most Z location error sector and the lower-most Z location error sector.*

*30. The imaging apparatus of claim 29 wherein the computer is further programmed to calculate the maximum Z location error in accordance with:*

*maximum_error_spread=maximum_error−minimum_error*

*where:*

*maximum_error represents the single-sector Z location error corresponding to the upper-most Z location error sector and minimum_error represents the single-sector Z location error corresponding to the lower-most Z location error sector.*

*31. The imaging apparatus of claim 29 wherein the computer is further programmed to determine the multiple-sector Z location error by calculating a weighted average Z location error based on the upper-most Z location error sector and the lower-most Z location error sector.*

*32. The imaging apparatus of claim 31 wherein the computer is further programmed to calculate the weighted average Z location error in accordance with:*

*WE=total error over all sectors/total view over all sectors*

*where:*

*WE represents the weighted average Z location error and total error over all sectors represents a total Z location error over all sectors.*

*33. An imaging method comprising:*

*accessing a predetermined number of sectors to reconstruct;*

*receiving scan data associated with the predetermined number of sectors;*

*determining a Z location error threshold;*

*determining a plurality of Z locations for a desired Z location corresponding to the predetermined number of sectors;*

*calculating a first multi-sector Z location error based on the plurality of Z locations;*

*reconstructing less than the predetermined number of sectors to create an image if the first multi-sector Z location error is above the Z location error threshold; otherwise*

*reconstructing the predetermined number of sectors to create an image.*

*34. The method of claim 33 further comprising:*

*determining a plurality of detector coverage limits, each detector coverage limit corresponding to a respective one of the predetermined number of sectors;*

*determining a plurality of single-sector Z location errors based on the plurality of detector coverage limits; and*

*calculating the first multi-sector Z location error based on the plurality of single-sector Z location errors.*

*35. The method of claim 33 wherein reconstructing less than the predetermined number of sectors further comprises:*

*calculating a second multi-sector Z location error based on the plurality of Z locations; and*

*reconstructing a set of sectors having one less sector than the predetermined number of sectors if the second multi-sector Z location error is below the Z location error threshold.*

*36. The method of claim 33 wherein calculating the first multi-sector Z location error comprises calculating a maximum Z location error and a weighted average Z location error based on the plurality of Z locations.*

*37. The method of claim 33 wherein calculating the maximum Z location error comprises determining a maximum error between an upper most sector and a lower most sector of the predetermined number of sectors.*

*38. The method of claim 36 wherein calculating the weighted average Z location error comprises determining an average Z location error weighted by a total view of the predetermined number of sectors.*

* * * * *

UNITED STATES PATENT AND TRADEMARK OFFICE

CERTIFICATE OF CORRECTION

PATENT NO. : RE 41,740 E
APPLICATION NO. : 11/706836
DATED : September 21, 2010
INVENTOR(S) : Okerlund et al.

It is certified that error appears in the above-identified patent and that said Letters Patent is hereby corrected as shown below:

Col. 4, line 16, delete "minimum error-max(*Zi*-" and substitute therefore
-- minimum error=max(*Zi*- --.

Col. 10, line 50 (Claim 37), delete "claim 33" and substitute therefore -- claim 36 --.

Signed and Sealed this

Thirtieth Day of November, 2010

David J. Kappos

David J. Kappos
*Director of the United States Patent and Trademark Office*